US010022177B2

(12) United States Patent
Ide

(10) Patent No.: US 10,022,177 B2
(45) Date of Patent: Jul. 17, 2018

(54) MEDICAL TREATMENT APPARATUS

(71) Applicant: OLYMPUS CORPORATION, Tokyo (JP)

(72) Inventor: Takayuki Ide, Fussa (JP)

(73) Assignee: OLYMPUS CORPORATION, Tokyo (JP)

( * ) Notice: Subject to any disclaimer, the term of this patent is extended or adjusted under 35 U.S.C. 154(b) by 1333 days.

(21) Appl. No.: 13/899,625

(22) Filed: May 22, 2013

(65) Prior Publication Data
US 2013/0253508 A1 Sep. 26, 2013

Related U.S. Application Data

(63) Continuation of application No. PCT/JP2011/078543, filed on Dec. 9, 2011.

(30) Foreign Application Priority Data

Dec. 14, 2010 (JP) .................................. 2010-278063

(51) Int. Cl.
*A61B 18/08* (2006.01)
*A61B 18/14* (2006.01)
*A61B 18/00* (2006.01)

(52) U.S. Cl.
CPC ............ *A61B 18/14* (2013.01); *A61B 18/085* (2013.01); *A61B 18/1445* (2013.01);
(Continued)

(58) Field of Classification Search
CPC ... A61B 18/14; A61B 18/085; A61B 18/1445; A61B 18/1442; A61B 18/1447;
(Continued)

(56) References Cited

U.S. PATENT DOCUMENTS 3,845,771 A * 11/1974 Vise ...................... A61B 18/14
606/49
5,443,463 A * 8/1995 Stern ........................ A61N 1/40
606/51
(Continued)

FOREIGN PATENT DOCUMENTS

JP 62-219953 A 9/1987
JP 2003-325537 A 11/2003
(Continued)

OTHER PUBLICATIONS

Hybond, Wire bonding development, May 2, 2009.*
(Continued)

*Primary Examiner* — Daniel Fowler
(74) *Attorney, Agent, or Firm* — Scully, Scott, Murphy & Presser, P.C.

(57) ABSTRACT

A medical treatment apparatus is an apparatus for treating a living body tissue by heating the living body tissue. The apparatus includes a heat transfer portion, a heating chip and a flexible substrate. The heat transfer portion is configured to come into contact with the living body tissue and transfer heat to the living body tissue. The heating chip is disposed on the heat transfer portion and is configured to heat the heat transfer portion. The flexible substrate is partly joined to a first surface of the heat transfer portion on which the heating chip is disposed, with a remaining portion extending outside the heat transfer portion. A heating trace for supplying power to the heating chip is formed on the flexible substrate.

17 Claims, 13 Drawing Sheets

(52) U.S. Cl.
CPC ............... *A61B 2018/00589* (2013.01); *A61B 2018/00595* (2013.01); *A61B 2018/00601* (2013.01); *A61B 2018/00791* (2013.01); *A61B 2018/1455* (2013.01); *A61B 2218/002* (2013.01)

(58) Field of Classification Search
CPC ........... A61B 2018/00589; A61B 2018/00595; A61B 2018/00601; A61B 2018/00791; A61B 2018/1455; A61B 2018/145; A61B 2018/1452; A61B 2018/1457; A61B 2218/002
See application file for complete search history.

(56) References Cited

U.S. PATENT DOCUMENTS

| | | | | |
|---|---|---|---|---|
| 5,443,470 A | * | 8/1995 | Stern | A61B 18/14 606/32 |
| 5,499,981 A | * | 3/1996 | Kordis | A61B 5/0422 606/41 |
| 5,558,672 A | * | 9/1996 | Edwards | A61B 18/148 604/22 |
| 5,916,213 A | * | 6/1999 | Haissaguerre | A61B 18/08 600/374 |
| 5,980,518 A | * | 11/1999 | Carr | A61B 18/1442 606/29 |
| 6,258,086 B1 | * | 7/2001 | Ashley | A61B 17/1671 604/510 |
| 6,511,478 B1 | * | 1/2003 | Burnside | A61B 18/1492 600/549 |
| 2003/0018331 A1 | * | 1/2003 | Dycus | A61B 18/1445 606/48 |
| 2008/0015575 A1 | * | 1/2008 | Odom | A61B 18/1445 606/51 |
| 2008/0262489 A1 | * | 10/2008 | Steinke | A61B 18/1492 606/33 |
| 2009/0270852 A1 | * | 10/2009 | Takashino | A61B 18/085 606/27 |

FOREIGN PATENT DOCUMENTS

| | | |
|---|---|---|
| JP | 2004-160191 A | 6/2004 |
| JP | 2004-329764 A | 11/2004 |
| JP | 2006-158517 A | 6/2006 |
| JP | 2009-247893 A | 10/2009 |

OTHER PUBLICATIONS

International Search Report dated Jan. 24, 2012 issued in PCT/JP2011/078543.
International Preliminary Report on Patentability together with the Written Opinion dated Jun. 27, 2013 received in related International Application No. PCT/JP2011/078543.

* cited by examiner

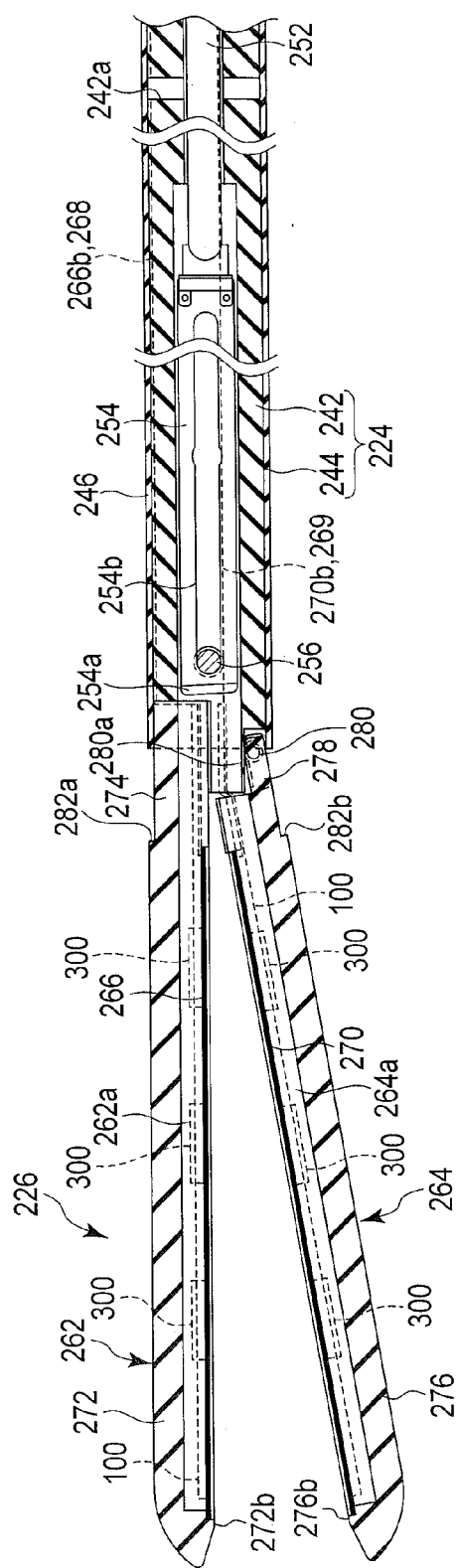
F I G. 2B

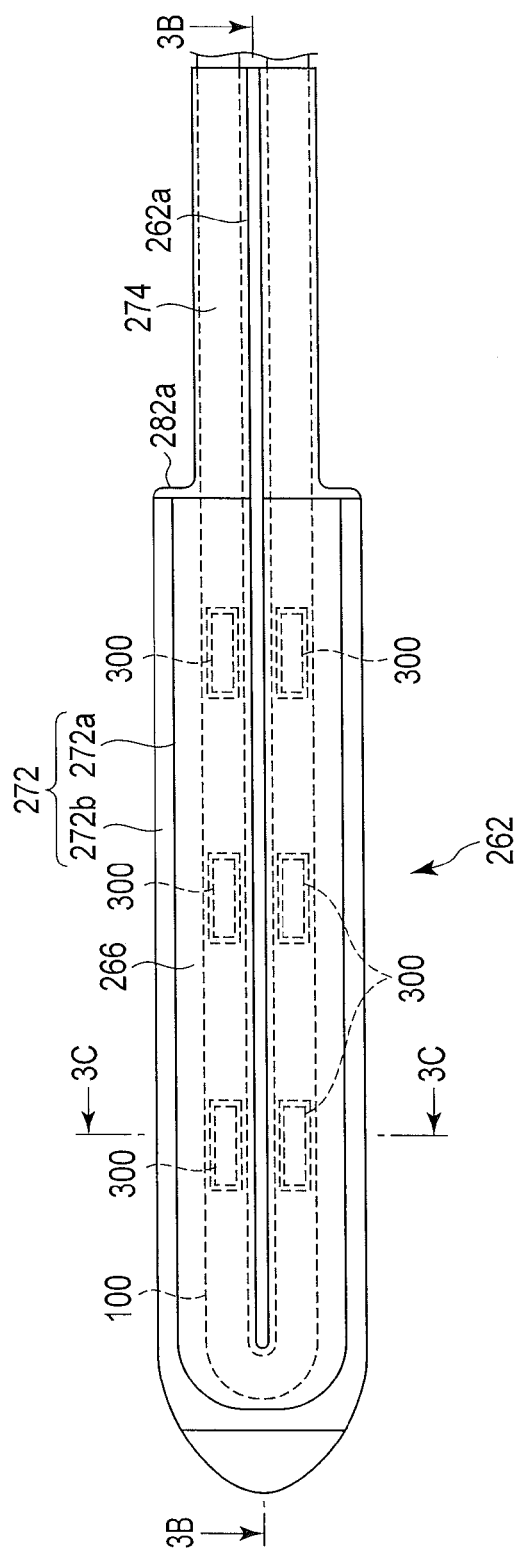
F I G. 3A

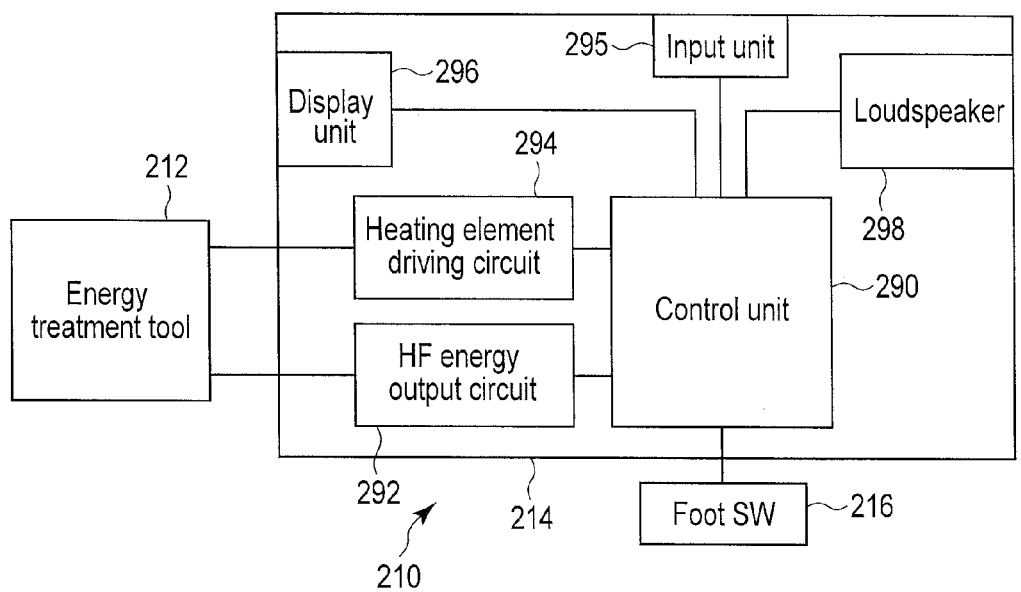
F I G. 6

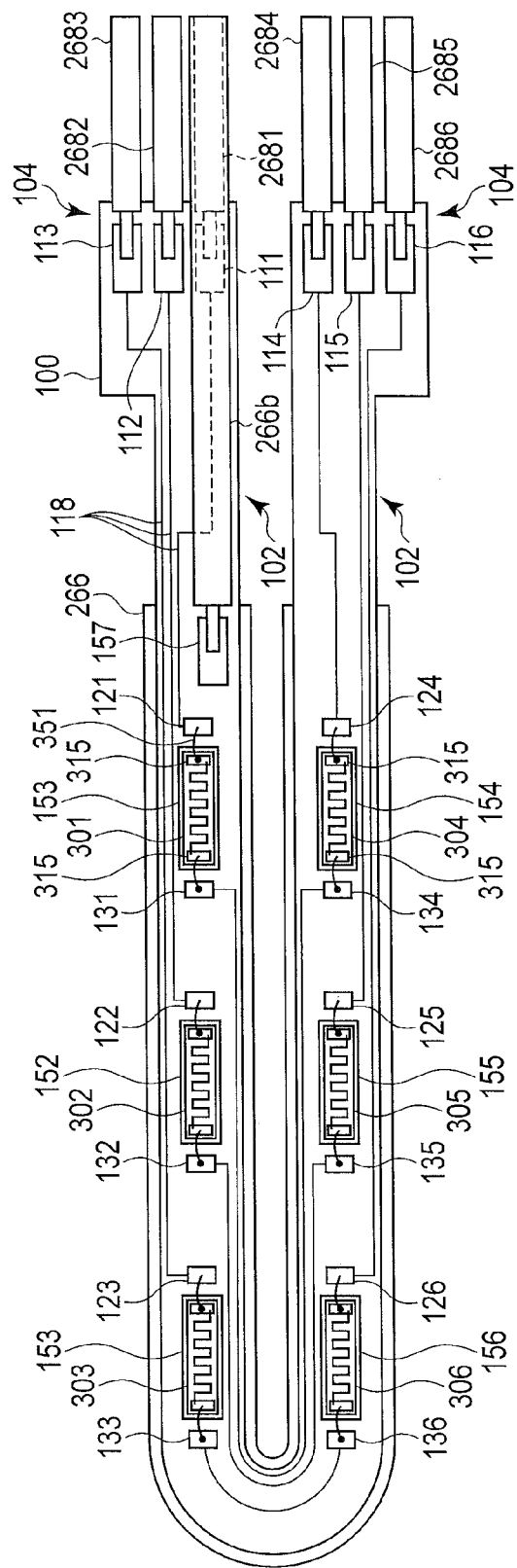
F I G. 9

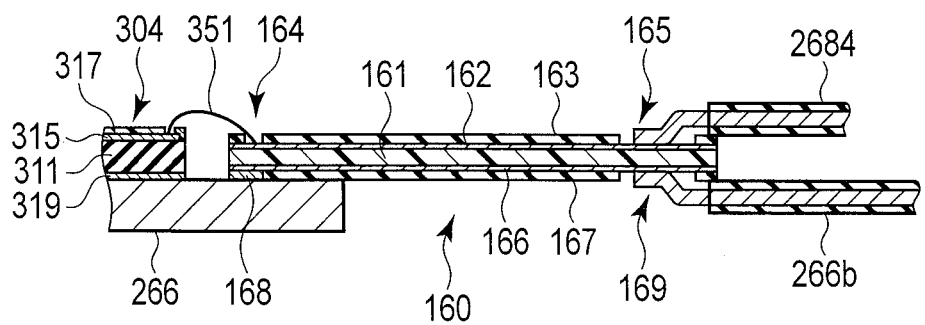
F I G. 10B

MEDICAL TREATMENT APPARATUS

CROSS REFERENCE TO RELATED APPLICATIONS

This application is a Continuation application of PCT Application No. PCT/JP2011/078543, filed Dec. 9, 2011 and based upon and claiming the benefit of priority from prior Japanese Patent Application No. 2010-278063, filed Dec. 14, 2010, the entire contents of all of which are incorporated herein by reference.

BACKGROUND OF THE INVENTION

1. Field of the Invention

The present invention relates to a medical treatment apparatus.

2. Description of the Related Art

In general, there is known a medical treatment apparatus which treats a living body tissue by using high-frequency energy or thermal energy. For example, Jpn. Pat. Appln. KOKAI Publication No. 2009-247893 discloses the following medical treatment apparatus. That is, this medical treatment apparatus includes an openable holding portion which grips a living body tissue to be treated. A portion of the holding portion which comes into contact with a living body tissue is provided with a high-frequency electrode for applying a high-frequency voltage and a heater member for heating the high-frequency electrode. The holding portion includes a cutter. When using such a medical treatment apparatus, the operator first grips a living body tissue with the holding portion and applies a high-frequency voltage to it. The operator anastomoses the living body tissue with the holding portion by heating the living body tissue with the holding portion. In addition, it is possible to excise the living body tissue with the cutter of the holding portion while a living body tissue end portion is joined.

BRIEF SUMMARY OF THE INVENTION

In the above medical treatment apparatus, lead wires which supply power to the heater members and the like mounted on a heat transfer portion which heats a living body tissue, for example, the high-frequency electrode of the holding portion, are required to have heat resistance because the heat transfer portion is heated to a high temperature. A method of routing these lead wires needs to consider the requirement for the downsizing of the holding portion including the heat transfer portion.

It is therefore an object of the present invention to provide a medical treatment apparatus with consideration given to the heat resistance and routing method of lead wires which supply power to the holding portion.

To achieve the above described object, according to an aspect of the invention, a medical treatment apparatus for treating a living body tissue by heating the living body tissue includes a heat transfer portion configured to come into contact with the living body tissue and transfer heat to the living body tissue; a heating chip disposed on the heat transfer portion and configured to heat the heat transfer portion; and a flexible substrate which is partly joined to a first surface of the heat transfer portion on which the heating chip is disposed, with a remaining portion extending outside the heat transfer portion, a heating trace for supplying power to the heating chip being formed on the flexible substrate.

The present invention can provide a medical treatment apparatus which gives consideration to the thermal resistance of lead wires for supplying power to the holding portion and a routing method because power is supplied to the holding portion by using a flexible substrate.

Advantages of the invention will be set forth in the description which follows, and in part will be obvious from the description, or may be learned by practice of the invention. The advantages of the invention may be realized and obtained by means of the instrumentalities and combinations particularly pointed out hereinafter.

BRIEF DESCRIPTION OF THE SEVERAL VIEWS OF THE DRAWING

The accompanying drawings, which are incorporated in and constitute a part of the specification, illustrate embodiments of the invention, and together with the general description given above and the detailed description of the embodiments given below, serve to explain the principles of the invention.

FIG. 2B is a schematic sectional view showing an example of the arrangement of the shaft and holding portion of the energy treatment tool according to the first embodiment, with the holding portion being open;

FIG. 3A is a plan view schematically showing an example of the arrangement of the first holding member of the holding portion according to the first embodiment;

FIG. 6 is a block diagram showing an example of the configuration of an energy source according to the first embodiment;

FIG. 9 is a view showing another example of an arrangement including the first high-frequency electrode, flexible substrates, heater members, and various types of wires according to the second embodiment;

FIG. 10B is a sectional view showing another example of an arrangement including the first high-frequency electrode, flexible substrates, heater members, and various types of wires according to the third embodiment.

DETAILED DESCRIPTION OF THE INVENTION

First Embodiment

Figure 1:
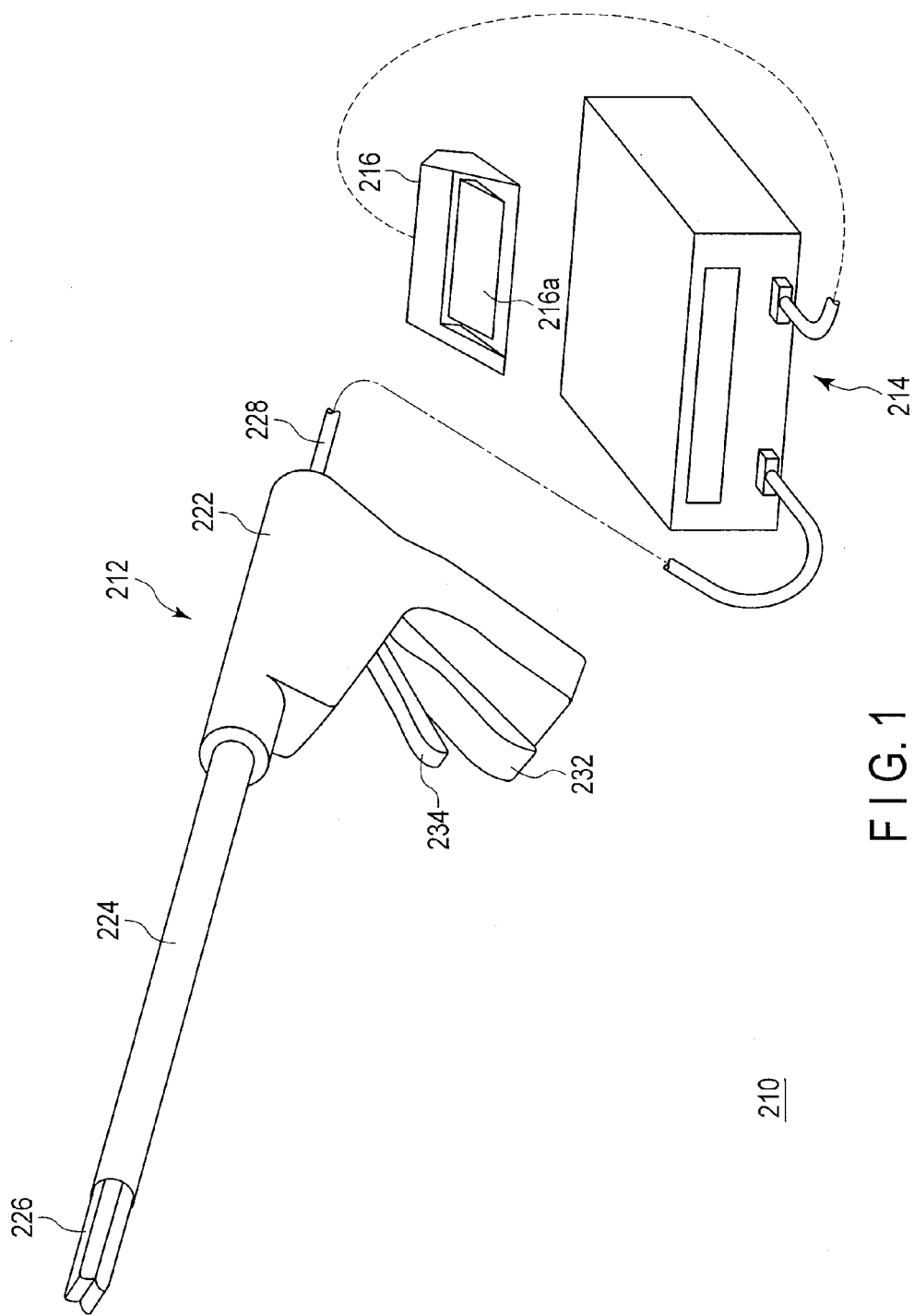
FIG. 1 is a schematic view showing an example of the arrangement of a medical treatment system according to the first embodiment of the present invention.

The first embodiment of the present invention will be described first with reference to the accompanying drawings. A medical treatment apparatus according to this embodiment is an apparatus which applies high-frequency energy and thermal energy to a living body tissue to treat the living body tissue. As shown in FIG. 1, a medical treatment apparatus 210 includes an energy treatment tool 212, an energy source 214, and a foot switch 216.

The energy treatment tool 212 is a linear-type surgical treatment tool for performing treatment upon penetrating through the abdominal wall. The energy treatment tool 212 includes a handle 222, a shaft 224, and a holding portion 226. The holding portion 226 is openable and serves as a treatment portion which performs treatment such as coagulation or incision while holding a living body tissue to be treated. The holding portion 226 is disposed on one end of the shaft 224. The other end of the shaft 224 is connected to the handle 222. For the sake of descriptive convenience, the holding portion 226 side and the handle 222 side will be referred to as the distal end side and the proximal end side, respectively. The handle 222 has a shape that allows the operator to easily grip, for example, an almost L shape. The handle 222 is connected to the energy source 214 via a cable 228. Obviously, the shape of the energy treatment tool 212 shown here is an example, and may have another shape as long as it has the same function. For example, the energy treatment tool 212 may have a forceps-like shape or have a curved shaft.

The foot switch 216 having a pedal 216a is connected to the energy source 214. The foot switch 216 which is operated by a foot of the operator may be replaced with a switch which is operated by a hand of the operator or another type of switch. The operator operates the pedal 216a of the foot switch 216 to ON/OFF-switch the energy source 214 to or not to supply energy to the energy treatment tool 212.

The handle 222 includes a holding portion opening/closing knob 232 and a cutter driving knob 234. The holding portion opening/closing knob 232 is coupled to the proximal end of a sheath 244 of the shaft 224 (to be described later). As the holding portion opening/closing knob 232 moves close and away from the handle 222, the sheath 244 moves along the axial direction of the shaft 224. As a consequence, the holding portion 226 opens and closes. The cutter driving knob 234 is a knob which is juxtaposed to the holding portion opening/closing knob 232 and moves a cutter 254 (to be described later).

Figure 2A:
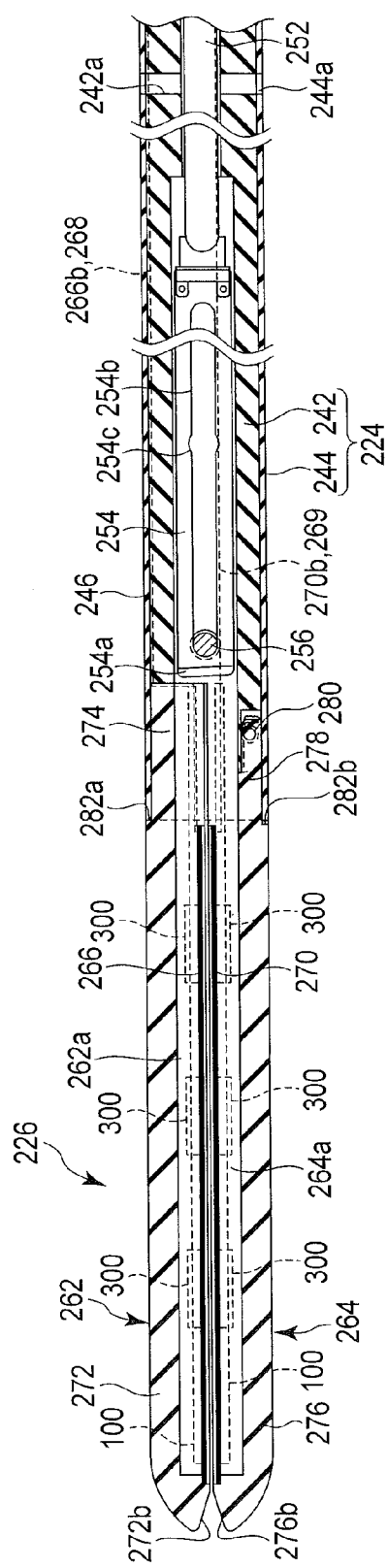
FIG. 2A is a schematic sectional view showing an example of the arrangement of the shaft and holding portion of an energy treatment tool according to the first embodiment, with a holding portion being closed.

FIGS. 2A and 2B each show an example of the structure of the holding portion 226 and shaft 224. FIG. 2A shows a state in which the holding portion 226 is closed. FIG. 2B shows a state in which the holding portion 226 is open. The shaft 224 includes a cylindrical body 242 and the sheath 244. The cylindrical body 242 is fixed to the handle 222 at the proximal end portion. As shown in FIGS. 2A and 2B, the sheath 244 is disposed on the outer circumference of the cylindrical body 242 so as to be slidable along the axial direction of the cylindrical body 242. The holding portion 226 is disposed on the distal end portion of the cylindrical body 242.

The holding portion 226 includes a first holding member 262 and a second holding member 264. The first and second holding members 262 and 264 each preferably have an insulation property as a whole. The first holding member 262 includes a first holding member main body 272 and a base portion 274 provided on the proximal end side of the first holding member main body 272. Likewise, the second holding member 264 integrally includes a second holding member main body 276 and a base portion 278 provided on the proximal end side of the second holding member main body 276. The base portion 274 of the first holding member 262 is fixed to the distal end portion of the cylindrical body 242 of the shaft 224. On the other hand, the base portion 278 of the second holding member 264 is pivotally supported on the distal end portion of the cylindrical body 242 of the shaft 224 by a support pin 280 disposed in a direction perpendicular to the axial direction of the shaft 224. The second holding member 264 pivots about the axis of the support pin 280 to open and close the first holding member 262.

The outer surface shapes of the first and second holding members 262 and 264 are smooth curved surfaces. While the second holding member 264 is closed relative to the first holding member 262, a sectional shape of the first and second holding member main bodies 272 and 276 in a joined state is almost circular or elliptic. In the closed state, a sectional shape of the base portion 274 of the first holding member 262 and the base portion 278 of the second holding member 264 is almost circular or elliptic. In this case, the diameter of the first and second holding member main bodies 272 and 276 is larger than that of the base portion 274 of the first holding member 262 and the base portion 278 of the second holding member 264. A stepped portion 282a is formed between the first holding member main body 272 and the base portion 274 of the first holding member 262. A stepped portion 282b is formed between the second holding member main body 276 and the base portion 278 of the second holding member 264.

An elastic member 280a, for example, a leaf spring, biases the second holding member 264 to open it relative to the first holding member 262. Sliding the sheath 244 to the distal end side relative to the cylindrical body 242 to cover the base portion 274 of the first holding member 262 and the base portion 278 of the second holding member 264 will close the first holding member 262 and the second holding member 264 against the biasing force of the elastic member 280a, as shown in FIG. 2A. On the other hand, sliding the sheath 244 to the proximal end of the cylindrical body 242 will open the second holding member 264 relative to the first holding member 262 owing to the biasing force of the elastic member 280a, as shown in FIG. 2B.

As shown in FIGS. 2A and 2B, the recess portion 246 is formed in the cylindrical body 242 along the axial direction of the cylindrical body 242. The first high-frequency electrode conducting line 266b connected to the first high-frequency electrode 266 (to be described later) and a plurality of heater member conducting lines 268 connected to heater members 300 as heating members via a flexible substrate 100 are disposed in the recess portion 246. Likewise, the second high-frequency electrode conducting line 270*b* connected to the second high-frequency electrode 270 (to be described later) and a plurality of heater member conducting lines 269 connected to the heater members 300 via the flexible substrate 100 extend through the cylindrical body 242.

A driving rod 252 is disposed in the cylindrical body 242 so as to be movable along the axial direction of the cylindrical body 242. The thin plate-like cutter 254 is disposed on the distal end side of the driving rod 252. The distal end side of the cutter 254 is a free end, on which a blade 254*a* is formed. The proximal end side of the cutter 254 is fixed to the driving rod 252. A long slit 254*b* is formed between the distal end side and proximal end side of the cutter 254. A movement regulation pin 256 extending in a direction perpendicular to the axial direction of the shaft 224 and the planar direction of the cutter 254 and fixed to the cylindrical body 242 extends through the long slit 254*b*. The proximal end side of the driving rod 252 to which the cutter 254 is fixed is connected to the cutter driving knob 234. Operating the cutter driving knob 234 will move the cutter 254 along the axial direction of the cylindrical body 242 through the driving rod 252. In this case, the cutter 254 moves while being regulated by the movement regulation pin 256 and the long slit 254*b*. Note that lock portions 254*c* for locking the movement regulation pin 256 and controlling the movement of the cutter 254 are formed at at least three positions at one end and the other end of the long slit 254*b* of the cutter 254 and between one end and the other end. When moving to the distal end side, the cutter 254 is fitted in a cutter guide groove 262*a* formed in the first holding member 262 (to be described later) and a cutter guide groove 264*a* formed in the second holding member 264.

In order to discharge water vapor, tissue fluid, and the like (to be described later), fluid discharge ports 242*a* and 244*a* are respectively formed on the proximal end sides of the cylindrical body 242 and sheath 244 such that the positions of the ports coincide with each other while the holding portion 226 is closed (the state in FIG. 2A). Although not shown here, the outer circumferential surface of the fluid discharge port 244*a* of the sheath 244 is preferably provided with a connection mouthpiece. Performing suction through the connection mouth piece causes fluids such as water vapor and a liquid discharged from a living body tissue to be discharged through the cutter guide grooves 262*a* and 264*a*, the interior of the cylindrical body 242, the fluid discharge port 242*a* of the cylindrical body 242, the fluid discharge port 244*a* of the sheath 244, and the connection mouthpiece. Although the fluid discharge ports 242*a* and 244*a* are preferably provided in the shaft 224, they may be provided in the handle 222.

Figure 3B:
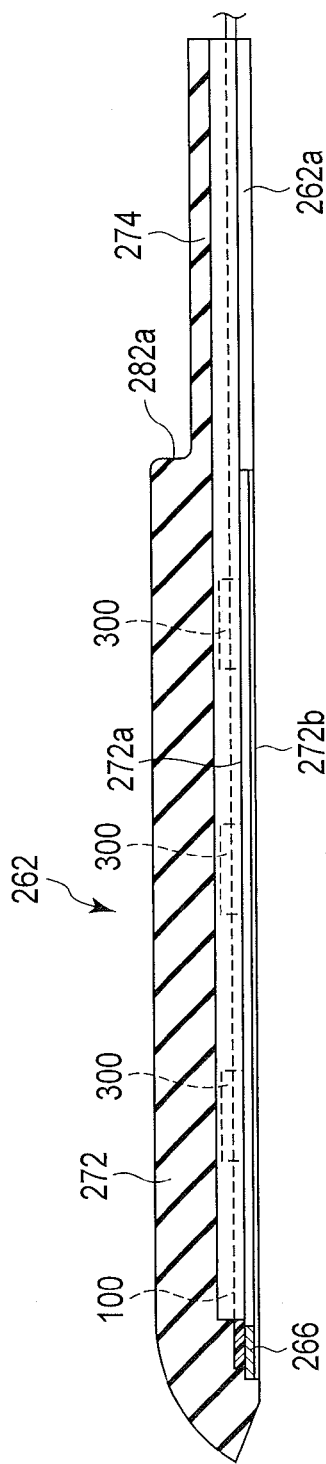
FIG. 3B is a schematic view showing an example of the arrangement of the first holding member of the holding portion according to the first embodiment, and is a longitudinal sectional view taken along line 3B-3B in FIG. 3A.
Figure 3C:
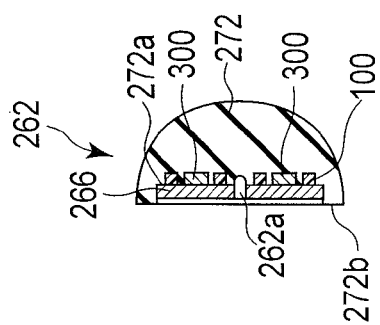
FIG. 3C is a schematic view showing an example of the arrangement of the first holding member of the holding portion according to the first embodiment, and is a cross-sectional view taken along line 3C-3C in FIG. 3A.

As shown in FIGS. 3A, 3B, and 3C, the cutter guide groove 262*a* for guiding the cutter 254 described above is formed in the first holding member main body 272 and the base portion 274. A recess portion 272*a* and a holding surface 272*b* including the edge portion of the recess portion 272*a* are formed on the first holding member main body 272. The first high-frequency electrode 266 formed from, for example, a thin copper plate is disposed in the recess portion 272*a*. Since the first high-frequency electrode 266 has the cutter guide groove 262*a*, its planar shape is almost U-shaped, as shown in FIG. 3A. The surface of the first high-frequency electrode 266 comes into contact with the living body tissue.

When the holding portion 226 is closed, the holding surface 272*b* comes into contact with a holding surface 276*b* of the second holding member 264 facing the holding surface 272*b* (to be described later). When the holding portion 226 is closed, the first high-frequency electrode 266 does not come into contact with the second high-frequency electrode 270 facing the first high-frequency electrode 266 (to be described later). While the holding portion 226 is closed, there is a gap between the first high-frequency electrode 266 and the second high-frequency electrode 270. However, since the living body tissue easily deforms, when the holding portion 226 in a closed state grips the living body tissue, the gripped living body tissue deforms in conformity with the gap and comes into contact with the first high-frequency electrode 266 and the second high-frequency electrode 270.

As shown in FIGS. 2A and 2B, the first high-frequency electrode 266 is electrically connected to the first high-frequency electrode conducting line 266*b*. The first high-frequency electrode 266 is connected to the cable 228 via the first high-frequency electrode conducting line 266*b*.

The cutter guide groove 264*a* is formed in the second holding member 264 at a position facing the cutter guide groove 262*a*. The cutter guide groove 262*a* of the first holding member 262 and the cutter guide groove 264*a* of the second holding member 264 can guide the cutter 254. The second holding member main body 276 is provided with the second high-frequency electrode 270 symmetrical in shape with the first high-frequency electrode 266 at a position facing the first high-frequency electrode 266. The second high-frequency electrode 270 is connected to the cable 228 via the second high-frequency electrode conducting line 270*b*.

Figure 4:
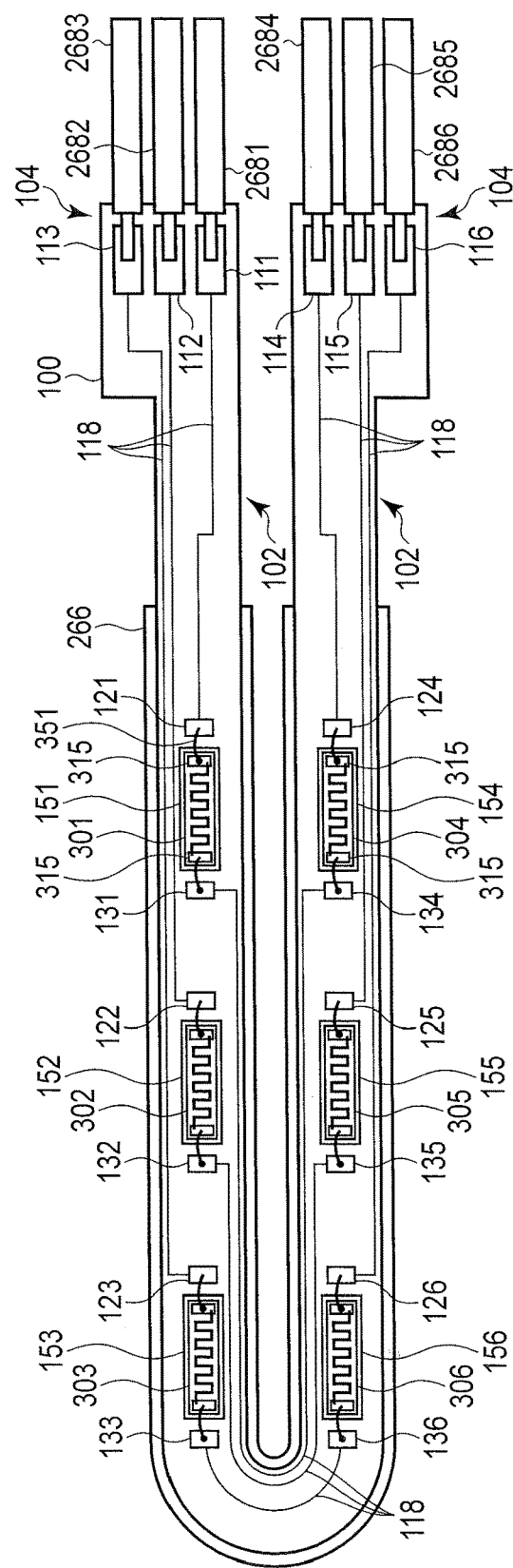
FIG. 4 is a view showing an example of an arrangement including the first high-frequency electrode, flexible substrates, heater members, and various types of wires according to the first embodiment.

The first and second holding member main bodies 272 and 276 each further have a mechanism for generating heat for cauterization of the living body tissue in contact with the first and second high-frequency electrodes 266 and 270. This mechanism will be described next. Note that the heating mechanism provided on the first holding member main body 272 has the same configuration as that provided on the second holding member main body 276. The heating mechanism provided on the first holding member main body 272 will therefore be exemplified below. As shown in FIG. 4, the flexible substrate 100 is disposed on the surface (rear surface) of the first high-frequency electrode 266 on the opposite side to the surface which comes into contact with the living body tissue. The flexible substrate 100 is a substrate obtained by printing copper traces on a substrate formed from, for example, polyimide. The flexible substrate 100 has an almost U shape in conformity with the shape of the first high-frequency electrode 266. Note, however, that a lead portion 102 extends longer, on the proximal end side, than the first high-frequency electrode 266.

The two end portions of the flexible substrate 100 on the proximal end side respectively have pad portions 104 formed wider than the remaining portions. Three electrodes are formed on each of the pad portions 104. The electrodes formed on one end portion will be sequentially referred to as electrodes 111, 112, and 113 from the cutter guide groove 262*a* side (inside). The electrodes formed on the other end portion will be sequentially referred to as electrodes 114, 115, and 116 from the cutter guide groove 262*a* side (inside).

Hole portions are formed in portions of the flexible substrate 100 which are located on the first high-frequency electrode 266, in threes at positions symmetric with respect to the cutter guide groove 262*a*, in the longitudinal direction of the first high-frequency electrode 266. These hole portions on the side of the cutter guide groove 262*a* on which the electrode 111 is formed will be sequentially referred to as hole portions 151, 152, and 153 from the proximal end side. These hole portions on the side of the cutter guide groove 262a on which the electrode 114 is formed will be sequentially referred to as hole portions 154, 155, and 156 from the proximal end side.

Figure 5A:
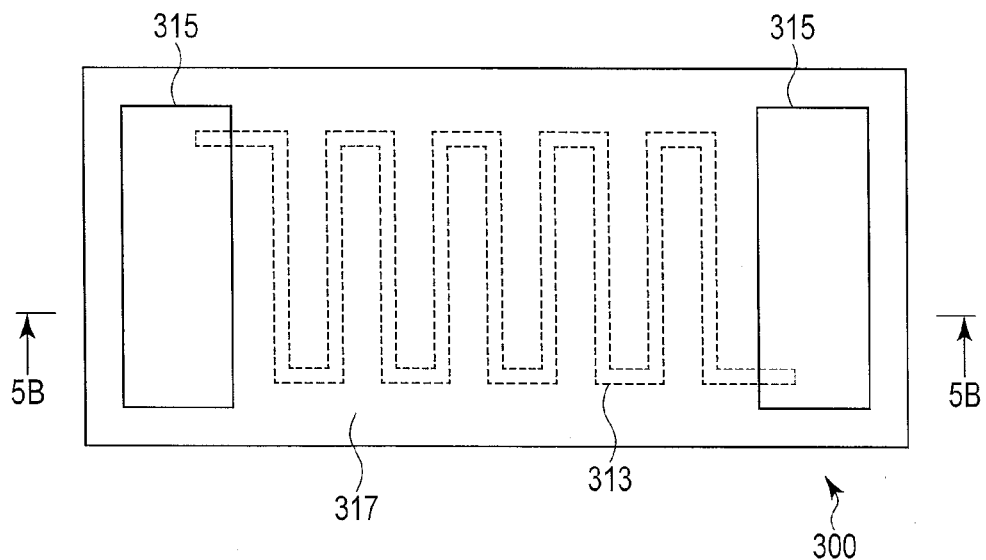
FIG. 5A is a plan view schematically showing an example of the arrangement of a heater member according to each embodiment.
Figure 5B:
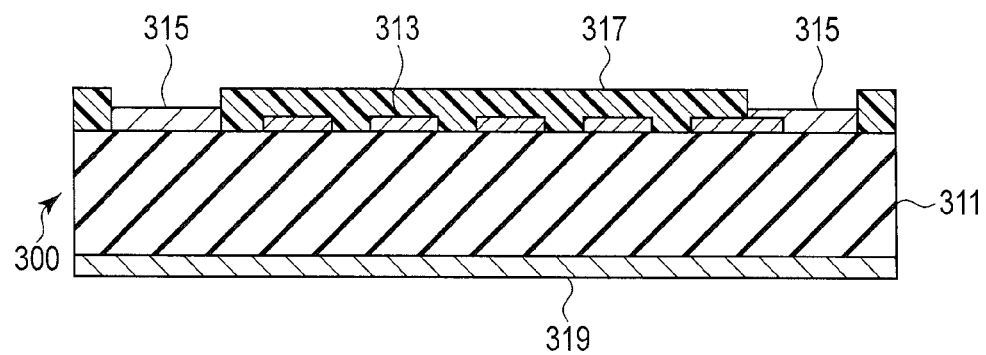
FIG. 5B is a view schematically showing an example of the arrangement of a heater member according to each embodiment, and is a sectional view taken along line 5B-5B in FIG. 5A.

The heater members 300 are respectively disposed at the positions of these six hole portions. The heater member 300 will be described with reference to FIGS. 5A and 5B. The heater member 300 is a heating member which generates heat. The heater member 300 is formed by using an alumina substrate 311. A resistance pattern 313 as a Pt thin film for heat generation is formed on the upper surface of the substrate 311, which is one of the principal surfaces. A pair of rectangular electrodes 315 respectively connected to the two ends of the resistance pattern 313 are formed on the upper surface of the substrate 311. A polyimide film 317 for insulation is formed on the upper surface of the substrate 311 including the surface of the resistance pattern 313, except for the portion on which the electrodes 315 are formed. A joining metal layer 319 is formed on the entire lower surface of the substrate 311. The electrodes 315 and the joining metal layer 319 are multilayer films formed from, for example, Ti, Cu, Ni, and Au. The electrodes 315 and the joining metal layer 319 have stable strength with respect to wire bonding and soldering. The joining metal layer 319 is provided to stabilize joining when soldering the heater member 300 to the first high-frequency electrode 266.

Each heater member 300 is fixed by soldering the upper surface of the joining metal layer 319 to the rear surface of the first high-frequency electrode 266. The flexible substrate 100 is provided with hole portions in accordance with the positions of the respective heater members 300. The heater member 300 corresponding to hole portion 151 will be referred to as a heater member 301. Likewise, the heater member 300 corresponding to hole portion 152 will be referred to as a heater member 302; the heater member 300 corresponding to hole portion 153, a heater member 303; the heater member 300 corresponding to hole portion 154, a heater member 304; the heater member 300 corresponding to hole portion 155, a heater member 305; and the heater member 300 corresponding to hole portion 156, a heater member 306.

As shown in FIG. 4, an electrode 121 is formed on the flexible substrate 100 at a position facing the electrode 315 disposed on the proximal end side of heater member 301. An electrode 131 is formed at a position facing the electrode 315 disposed on the distal end side of heater member 301. Likewise, electrodes 122, 123, 124, 125, and 126 are respectively formed at positions facing the electrodes 315 disposed on the proximal end sides of heater members 302, 303, 304, 305, and 306. Electrodes 132, 133, 134, 135, and 136 are respectively formed at positions facing the electrodes 315 disposed on the distal end sides of heater members 302, 303, 304, 305, and 306.

A trace 118 is printed on the flexible substrate 100 to connect electrodes 111 and 121 to each other. Likewise, traces 118 are printed on the flexible substrate 100 to connect electrodes 112 and 122 to each other, electrodes 113 and 123 to each other, electrodes 114 and 124 to each other, electrodes 115 and 125 to each other, and electrodes 116 and 126 to each other.

A trace 118 is printed on the flexible substrate 100 to connect electrodes 131 and 134 to each other. Likewise, traces 118 are printed on the flexible substrate 100 to connect electrodes 132 and 135 to each other and electrodes 133 and 136 to each other.

One of the plurality of heater member conducting lines 268 as general lead wires is connected to electrode 111. In this case, the heater member conducting line 268 connected to electrode 111 will be referred to as a heater member conducting line 2681. Likewise, a heater member conducting line 2682 as one of the plurality of heater member conducting lines 268 is connected to electrode 112. Likewise, a heater member conducting line 2683 is connected to electrode 113; a heater member conducting line 2684 is connected to electrode 114; a heater member conducting line 2685 is connected to electrode 115; a heater member conducting line 2686 is connected to electrode 116.

Electrode 121 on the flexible substrate 100 is connected to the electrode 315 disposed on the proximal end side of heater member 301 facing the electrode 121 via the wire 351 by wire bonding. Likewise, the electrodes 122, 123, 124, 125, 126, 131, 132, 133, 134, 135, and 136 on the flexible substrate 100 are respectively connected to the electrodes 315 on the heater members 300 facing them via the wires 351 by wire bonding.

With the above connection, heater member conducting line 2681, the resistance pattern 313 of heater member 301, the resistance pattern 313 of heater member 304, and heater member conducting line 2684 are connected in series in the order named. Likewise, heater member conducting line 2682, the resistance pattern 313 of heater member 302, the resistance pattern 313 of heater member 305, and heater member conducting line 2685 are connected in series in the order named. In addition, heater member conducting line 2683, the resistance pattern 313 of heater member 303, the resistance pattern 313 of heater member 306, and heater member conducting line 2686 are connected in series in the order named.

Supplying currents to heater members 301 and 304 via heater member conducting lines 2681 and 2684 can heat the proximal end side of the first high-frequency electrode 266 at which heater members 301 and 304 are located. Likewise, supplying currents to heater members 303 and 306 via heater member conducting lines 2683 and 2686 can heat the distal end side of the first high-frequency electrode 266. Likewise, supplying currents to heater members 302 and 305 via heater member conducting lines 2682 and 2685 can heat the intermediate portion of the first high-frequency electrode 266.

The first high-frequency electrode conducting line 266b for applying a high-frequency voltage to the first high-frequency electrode 226 from the cable 228 can be connected to an arbitrary portion on which the first high-frequency electrode 266 is exposed.

Note that in this embodiment, the heater member 300 has, for example, a length of about 3 mm and a width of about 1.2 mm. In addition, the first high-frequency electrode 266 has, for example, a length of about 35 mm in the longitudinal direction and a width of about 7 mm. The cutter guide groove 262a having a width of about 1 mm is cut in the first high-frequency electrode 266 along its central axis.

As shown in FIG. 6, a control unit 290, a high-frequency (HF) energy output circuit 292, a heating element driving circuit 294, an input unit 295, a display unit 296, and a loudspeaker 298 are arranged in the energy source 214. The high-frequency energy output circuit 292, the heating element driving circuit 294, the input unit 295, the display unit 296, and the loudspeaker 298 are connected to the control unit 290. The control unit 290 controls the respective units of the energy source 214. The high-frequency energy output circuit 292 is connected to the energy treatment tool 212, and drives the first and second high-frequency electrodes 266 and 270 of the energy treatment tool 212 under the control of the control unit 290. The heating element driving circuit 294 is connected to the energy treatment tool 212, and drives the heater members 300 of the energy treatment tool 212 under the control of the control unit 290. The foot switch (SW) 216 is connected to the control unit 290. The foot switch 216 inputs an ON signal and an OFF signal into the control unit 290, the ON signal indicating the energy treatment tool 212 performs treatment and the OFF signal indicating the energy treatment tool 212 stops treatment. The input unit 295 inputs various types of settings to the control unit 290. The display unit 296 displays various types of settings for the control unit 290. The loudspeaker 298 outputs an alarm sound and the like.

Note that the high-frequency energy output circuit 292 can output high-frequency energy and detects an impedance Z. That is, the high-frequency energy output circuit 292 has a sensor function of measuring the impedance Z of the living body tissue between the first and second high-frequency electrodes 266 and 270 of the energy treatment tool 212. The heating element driving circuit 294 supplies energy to the heater members 300 to cause them to generate heat, and has a sensor function of measuring a heating temperature T of the heater members 300.

The operation of the medical treatment apparatus 210 according to this embodiment will be described next. The operator operates the input unit 295 of the energy source 214 in advance to set output conditions for the medical treatment apparatus 210. More specifically, the operator sets a set power Pset [W] for a high-frequency energy output, a set temperature Tset [° C.] for a thermal energy output, thresholds Z1 and Z2 of impedance Z of the living body tissue, and the like in advance. This apparatus may be configured to individually set the respective values or select a set of set values in accordance with an operative method.

The operator inserts the holding portion 226 and shaft 224 of the energy treatment tool 212 into the abdominal cavity through, for example, the abdominal wall while the holding portion 226 is closed as shown in FIG. 2A. When the holding portion 226 approaches the living body tissue to be treated, the operator operates the holding portion opening/closing knob 232 of the handle 222 to open/close the first and second holding members 262 and 264 to grip the living body tissue to be treated. That is, first of all, the operator moves the sheath 244 to the proximal end side relative to the cylindrical body 242. As a consequence, the second holding member 264 opens relative to the first holding member 262 owing to the biasing force of the elastic member 280a.

While the holding portion 226 is open, the living body tissue is placed between the first holding member 262 and the second holding member 264. In this state, the operator moves the sheath 244 to the distal end side relative to the cylindrical body 242. As a consequence, the 244 closes the second holding member 264 relative to the first holding member 262 against the biasing force of the elastic member 280a. In this manner, the holding portion 226 grips the living body tissue to be treated together with the first and second holding members 262 and 264. At this time, the living body tissue to be treated is in contact with both the first high-frequency electrode 266 provided for the first holding member 262 and the second high-frequency electrode 270 provided for the second holding member 264.

When gripping the living body tissue to be treated with the holding portion 226, the operator operates the foot switch 216. When the operator switches the foot switch 216 to ON, the energy source 214 supplies high-frequency power with the set power Pset [W] set in advance to the first and second high-frequency electrodes 266 and 270 via the cable 228. The supplied power is, for example, about 20 to 80 W.

In this manner, a high-frequency current flows in the living body tissue to be treated which is gripped between the first holding member 262 and the second holding member 264. As a result, the living body tissue is heated and cauterized (denatured).

At the time of tissue cauterization, fluids (for example, a liquid such as blood and/or water vapor) are discharged from the living body tissue. At this time, the holding surface 272b of the first holding member 262 and the holding surface 276b of the second holding member 264 protrude from the first and second high-frequency electrodes 266 and 270. For this reason, holding surface 272b and holding surface 276b function as barrage portions (dams) to keep the fluids inside the first and second holding members 262 and 264.

Performing suction through the fluid discharge port 244a of the sheath 244 and the fluid discharge port 242a of the cylindrical body 242 will make the fluids staying in the first and second holding members 262 and 264 flow in the cutter guide grooves 262a and 264a and the cylindrical body 242. The fluids are then discharged from the fluid discharge port 242a and the fluid discharge port 244a. While fluids are discharged from the living body tissue, the fluids are kept discharged in the above manner. This prevents the occurrence of thermal spreading due to fluids discharged from the living body tissue with raised temperature, and hence can prevent the fluids from affecting portions which are not to be treated.

After the supply of high-frequency power stops, the energy source 214 supplies power to each heater member 300 to set its temperature to the temperature Tset [° C.] set in advance. In this case, the set temperature Tset is, for example, 100 to 300° C. At this time, a current flows from the energy source 214 to the resistance pattern 313 of the heater member 300 via the cable 228, heater member conducting line 268, heater member conducting line 269, and the wire 351 by wire bonding. The resistance pattern 313 generates heat. The heat generated by the resistance pattern 313 is conducted to the first high-frequency electrode 266 and the second high-frequency electrode 270 via the substrate 311 and the joining metal layer 319. As a result, the first and second high-frequency electrodes 266 and 270 rise in temperature, and the living body tissue in contact with the first and second high-frequency electrodes 266 and 270 is coagulated.

When the living body tissue is coagulated, the operator stops outputting thermal energy. Finally, the operator operates the cutter driving knob 234. As a consequence, the cutter 254 moves in the cutter guide grooves 262a and 264a to cut the living body tissue. With the above operation, the apparatus completes treatment of the living body tissue.

As described above, the first high-frequency electrode 266 or the second high-frequency electrode 270 functions as a heat transfer portion configured to come into contact with the living body tissue and transfer heat to the living body tissue. For example, the holding portion 226 functions as a holding member which grips the living body tissue. For example, the heater member 300 functions as a heating chip which heats the heat transfer portion. For example, the flexible substrate 100 functions as a flexible substrate on which heating trace for supplying power to heating chips are formed. For example, the pad portion 104 functions as a lead wire connection portion for the connection of a heating lead wire for supplying power to a heating trace.

This embodiment can adjust input power for the heater members 300 arranged in each of zones such as the distal end portion, intermediate portion, and proximal end portion of the first high-frequency electrode 266 or second high-frequency electrode 270. This makes it possible to perform temperature control for each zone even if a living body tissue to be heated is in contact with some portions of the first high-frequency electrode 266 or second high-frequency electrode 270 and is not in contact with the other portions, thereby accurately performing temperature control.

It is possible to use a wire bonder used for the general manufacture of semiconductor devices to perform wire bonding to connect each electrode on the flexible substrate 100 to the electrode 315 of the heater member 300. The manufacture using a wire bonder exhibits very high productivity and can be performed at a low cost. As described above, the arrangement of this embodiment based on traces using the flexible substrate 100 and wire bonding is effective especially when it is necessary to route many wires on the first and second high-frequency electrodes 266 and 270 as in the embodiment which can perform temperature control for each zone.

In addition, the flexible substrate 100 is formed from polyimide with copper traces being printed on it, and hence has excellent thermal resistance. As in the embodiment, the lead portion 102 is made to have a length long enough to avoid the influence of heat generated by the first and second high-frequency electrodes 266 and 270. This makes the heater member conducting lines 268 and 269 respectively connected to the first and second high-frequency electrodes 266 and 270 less susceptible to the influence of heat generated by the first and second high-frequency electrodes 266 and 270. This makes it unnecessary to improve heat resistance. Therefore, it is possible to use inexpensive lead wires for the heater member conducting lines 268 and 269.

In addition, the lead portion 102 is part of the flexible substrate 100, and is rich in flexibility to facilitate routing of wires. Furthermore, since the size of the pad portion 104 can be designed regardless of the size of the first high-frequency electrode 266, it is possible to ensure a large region connected to a lead wire. That is, it is possible to downsize the first and second high-frequency electrodes 266 and 270 without any consideration to a connection region for lead wires.

Modification of First Embodiment

A modification of the first embodiment of the present invention will be described next. This modification will be described below with reference to differences from the first embodiment. The same reference numerals denote the same parts, and a description of them will be omitted. In the first embodiment, the first high-frequency electrode conducting line 266b for applying a high-frequency voltage to the first high-frequency electrode 266 is connected to an arbitrary portion on which the first high-frequency electrode 266 is exposed. In contrast to this, in this modification, electrodes and wires are provided on the flexible substrate 100 to connect the first high-frequency electrode conducting line 266b to the first high-frequency electrode 266.

Figure 7:
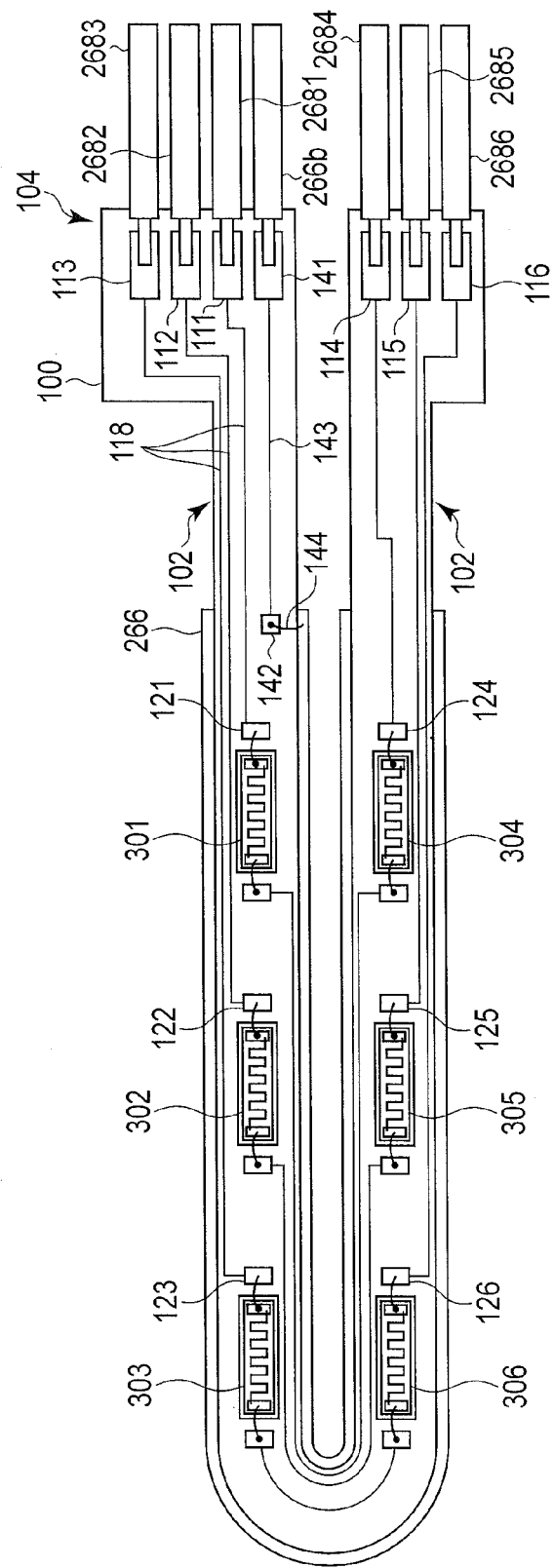
FIG. 7 is a view showing an example of an arrangement including the first high-frequency electrode, flexible substrates, heater members, and various types of wires according to the first embodiment.

As shown in FIG. 7, the flexible substrate 100 according to this modification includes, in addition to the various types of electrodes and wires on the flexible substrate 100 according to the first embodiment, an electrode 141 to be connected to the first high-frequency electrode conducting line 266b, an electrode 142 to be connected to the first high-frequency electrode 266, and a wire 143 which connects the electrode 141 to the electrode 142. The first high-frequency electrode 266 is connected to the electrode 142 via a wire 144. As described above, the wire 143 functions as a high-frequency wire for supplying high-frequency power to the heat transfer portion. The second high-frequency electrode 270 can have the same arrangement.

According to this embodiment, it is possible to mount, on the single flexible substrate 100, the connection wires to the respective heater members 300 on the first high-frequency electrode 266 and the lead wire portions for supplying power to the first high-frequency electrode 266. Likewise, it is possible to form, on the single flexible substrate 100, the connection wires to the respective heater members 300 on the second high-frequency electrode 270 and the lead wire portions for supplying power to the second high-frequency electrode 270. In addition, this modification can also obtain the same effects as those of the first embodiment. That is, there is no need to consider the heat resistance of the heater member conducting lines 268 and 269 and of the first and second high-frequency electrode conducting lines 266b and 270b. In addition, there is no need to consider connection regions for lead wires. This makes it possible to downsize the first and second high-frequency electrodes 266 and 270.

Second Embodiment

Figure 8:
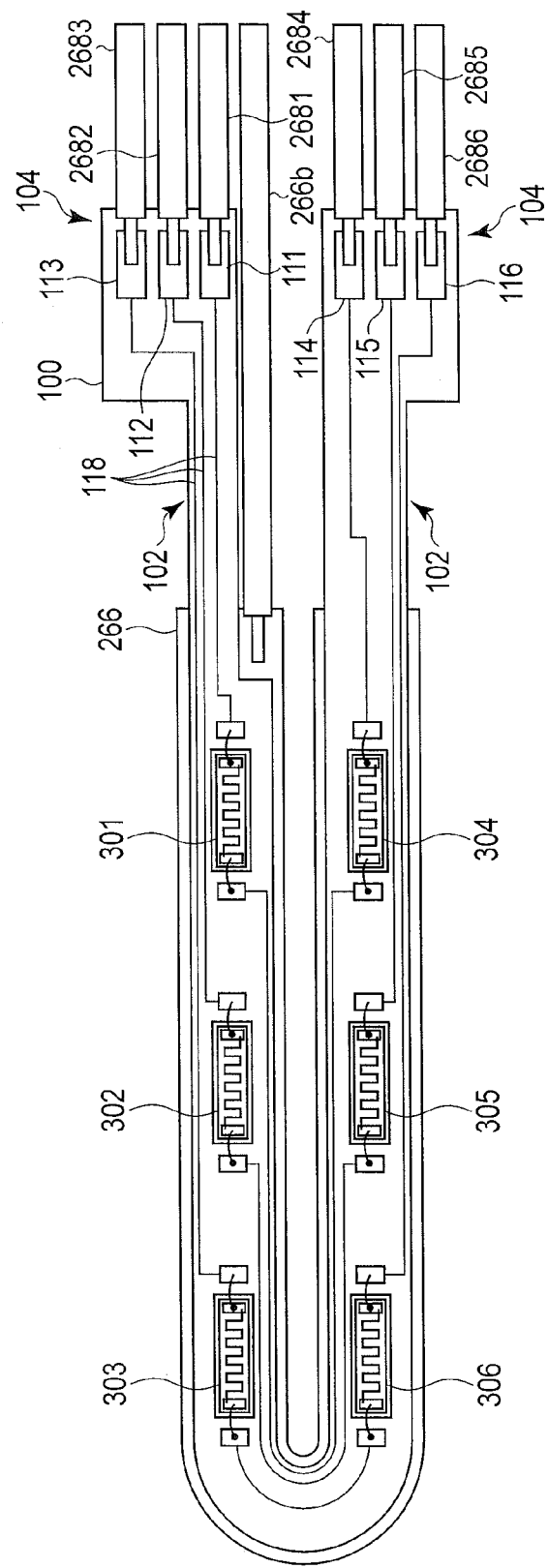
FIG. 8 is a view showing an example of an arrangement including the first high-frequency electrode, flexible substrates, heater members, and various types of wires according to the second embodiment.

The second embodiment of the present invention will be described next. This embodiment will be described below with reference to differences from the first embodiment. The same reference numerals denote the same parts, and a description of them will be omitted. In addition, a first high-frequency electrode 266 and a second high-frequency electrode 270 have the same configuration, and hence the first high-frequency electrode 266 will be exemplified. In the embodiment, as shown in FIG. 8, a first high-frequency electrode conducting line 266b for applying a high-frequency voltage to the first high-frequency electrode 266 is located on the proximal end side of the first high-frequency electrode 266 and connected to a portion near a cutter guide groove 262a.

Disposing the first high-frequency electrode conducting line 266b on the proximal end side of the first high-frequency electrode 266 at a position near the cutter guide groove 262a makes a flexible substrate 100 have a width smaller than that of the first high-frequency electrode 266 at a portion to which the first high-frequency electrode conducting line 266b is connected.

In this manner, the first high-frequency electrode conducting line 266b is connected to the surface on which the heating chips of the heat transfer portions are arranged and functions as a high-frequency electrode lead wire for supplying high-frequency power to the heat transfer portions. For example, the flexible substrate 100 is shaped to detour the portion to which the high-frequency electrode lead wire is connected.

In this embodiment as well, making a lead portion 102 have a length long enough to avoid the influence of heat generated by the first high-frequency electrode 266 obviates the need to consider the heat resistance of heater member conducting lines 2681, 2682, 2683, 2684, 2685, and 2686. In addition, the embodiment can obtain the same effects as those of the first embodiment concerning the heater member conducting lines 2681, 2682, 2683, 2684, 2685, and 2686.

In addition, in this embodiment, when, in particular, applying a high voltage to the first high-frequency electrode 266, it is possible to use a lead wire having a strength high enough to resist the high voltage. In this case, since the width of the flexible substrate 100 is smaller than that of the first high-frequency electrode 266, it is possible to ensure a sufficient space. This increases the degree of freedom of design, for example, designing to increase the thickness of the first high-frequency electrode conducting line 266*b*. The first high-frequency electrode conducting line 266*b* is located near the first high-frequency electrode 266, and hence tends to be exposed to heat. In this case, however, the heat resistance of the first high-frequency electrode conducting line 266*b* may be increased accordingly. Note that since the first high-frequency electrode 266 requires only one first high-frequency electrode conducting line 266*b*, almost no problem arises in terms of space and cost as compared with a case in which a plurality of heater member conducting lines are required.

The shape of the flexible substrate 100 is not limited to that shown in FIG. 8. As shown in FIG. 9, a hole 157 may be provided in a portion of the flexible substrate 100, and the first high-frequency electrode conducting line 266*b* may be connected to the first high-frequency electrode 266 in the hole 157. In this case as well, the same effects as those described above can be obtained.

Third Embodiment

Figure 10A:
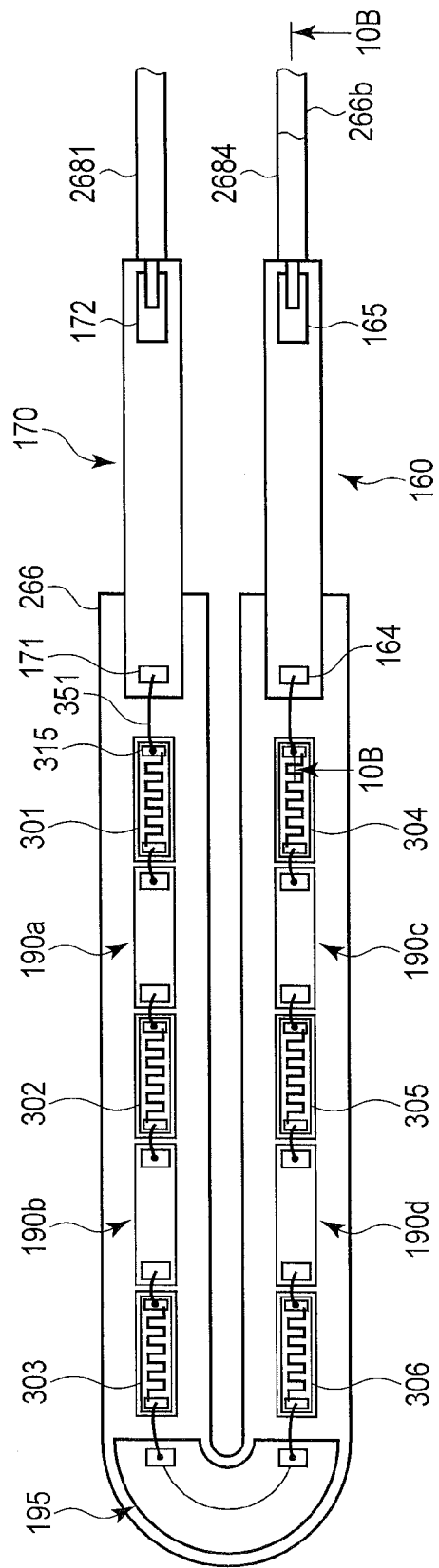
FIG. 10A is a a view showing an example of an arrangement including the first high-frequency electrode, flexible substrates, heater members, and various types of wires according to the third embodiment.

The third embodiment of the present invention will be described next. This embodiment will be described below with reference to differences from the first embodiment. The same reference numerals denote the same parts, and a description of them will be omitted. In addition, a first high-frequency electrode 266 and a second high-frequency electrode 270 have the same configuration, and hence the first high-frequency electrode 266 will be exemplified. In the embodiment, as shown in FIG. 10A, heater members 301, 302, 303, 304, 305, and 306 are arranged on the first high-frequency electrode 266 as in the first embodiment. A first flexible substrate 160 is disposed on one of the two sides of a cutter guide groove 262*a* in the proximal end of the first high-frequency electrode 266, and a second flexible substrate 170 is disposed on the other side.

The first flexible substrate 160 will be described with reference to the sectional view shown in FIG. 10B. The first flexible substrate 160 includes a substrate 161. A first trace layer 162 made of a metal is formed on one surface of the substrate 161. A first insulating layer 163 is stacked on the first trace layer 162. In this case, the distal end side of the first flexible substrate 160 includes a rectangular region on which the first insulating layer 163 is not stacked. In this region, a first terminal 164 is formed, which can be connected to the first trace layer 162 because it is exposed. Likewise, the proximal end side of the first flexible substrate 160 includes a rectangular region on which the first insulating layer 163 is not stacked. In this region, a second terminal 165 is formed, which can be connected to the first trace layer 162 because it is exposed.

A second trace layer 166 is formed on the surface of the substrate 161 on the opposite side to the surface on which the first trace layer 162 is formed. A second insulating layer 167 is stacked on the second trace layer 166. In this case, a metal layer is formed on a portion of the distal end side of the first flexible substrate 160 instead of the second insulating layer 167 to form a third terminal 168. The proximal end side of the first flexible substrate 160 includes a rectangular region on which the second insulating layer 167 is not stacked. In this region, a fourth terminal 169 is formed, which can be connected to the second trace layer 166 because it is exposed.

The first flexible substrate 160 is joined to the surface of the first high-frequency electrode 266 to which the heater members 301 and the like are joined. In this case, the first high-frequency electrode 266 and the third terminal 168 are joined to each other with a conductive joining material such as solder so as to face each other and be electrically connected to each other. The first terminal 164 of the first flexible substrate 160 is electrically connected to a electrode 315 of the heater member 304 via a wire 351 by wire bonding. A heater member conducting line 2684 is connected to the first trace layer 162 as part of the second terminal 165. A first high-frequency electrode conducting line 266*b* is connected to the second trace layer 166 of the fourth terminal 169.

As described above, the heater member conducting line 2684 is electrically connected to the electrode 315 of the heater member 304 via the first trace layer 162. The first high-frequency electrode conducting line 266*b* is electrically connected to the first high-frequency electrode 266 via the second trace layer 166.

Like the first flexible substrate 160, a trace layer and an insulating layer are formed on one surface of the second flexible substrate 170. A terminal 171 which can be connected to the trace layer because no insulating layer is stacked on it is formed on a portion of the distal end portion of the second flexible substrate 170. Likewise, a terminal 172 which can be connected to the trace layer because no insulating layer is stacked on it is formed on a portion of the proximal end portion of the second flexible substrate 170. The second flexible substrate 170 is joined to the first high-frequency electrode 266 on the surface on the opposite side to the surface on which the terminals 171 and 172 are formed. The heater member conducting line 2681 is connected to the terminal 172. The terminal 171 is electrically connected to the electrode 315 of the heater member 301 via the wire 351 by wire bonding. Therefore, the heater member conducting line 2681 is electrically connected to the electrode 315 of the heater member 301 via the trace layer on the second flexible substrate 170.

A flexible substrate 190*a* having the same structure as that of the second flexible substrate 170 and an appropriate size is joined between the heater member 301 and the heater member 302 on the first high-frequency electrode 266. An electrode of the heater member 301 and a terminal of the flexible substrate 190*a* which faces the electrode are electrically connected to each other via the wire 351 by wire bonding. Likewise, an electrode of the heater member 302 and a terminal of the flexible substrate 190*a* which faces the electrode are electrically connected to each other via the wire 351 by wire bonding. Therefore, the electrodes of the heater member 301 and heater member 302 which are located close to each other are connected via the trace layer on the flexible substrate 190*a*.

Likewise, a flexible substrate 190*b* is disposed between the heater member 302 and the heater member 303. A flexible substrate 190*c* is disposed between the heater member 304 and the heater member 305. A flexible substrate 190*d* is disposed between the heater member 305 and the heater member 306. The heater members are connected to each other via these flexible substrates. A flexible substrate 195 having the same structure as that of the second flexible substrate 170 and complying with the shape of the distal end portion of the first high-frequency electrode 266 is joined to the distal end portion of the first high-frequency electrode 266. The heater members 303 and 306 are connected to each other via the trace layer on the flexible substrate 195 in the same manner as described above.

In the above manner, the heater members 301, 302, 303, 306, 305, and 304 are connected in series. The heater member conducting lines 2681 and 2684 are respectively connected to the two ends of the above series circuit. This embodiment can heat the first high-frequency electrode 266 by simultaneously applying voltages to the six heater members 301, 302, 303, 304, 305, and 306 via the heater member conducting lines 2681 and 2684. The embodiment can also apply a high-frequency voltage to the first high-frequency electrode 266 from the first high-frequency electrode conducting line 266*b* via the second trace layer 166.

In this manner, the first trace layer 162 functioning as a heating wire is formed on, for example, one of the principal surfaces of the flexible substrate 100, and the second trace layer 166 functioning as the above high-frequency wire is formed on the other principal surface of the flexible substrate 100. The surface on which the heating chips of the heat transfer portions and the surface on which the high-frequency wires of the flexible substrates are formed face each other and are joined to each other such that the heat transfer portions are electrically connected to the high-frequency wires.

If, for example, the heater member conducting line 2684 is connected to the first high-frequency electrode conducting line 266*b* on the same surface of the flexible substrate as in the modification of the first embodiment, it is necessary to separately provide a wire from the trace layer connected to the first high-frequency electrode conducting line 266*b* to the first high-frequency electrode 266 like, for example, the wire 144 in FIG. 7. In contrast to this, in this embodiment, since the surface for the connection of the heater member conducting line 2684 and the surface for the connection of the first high-frequency electrode conducting line 266*b* are the upper and lower surfaces, wiring can be omitted.

In addition, in this embodiment as well, making the first flexible substrate 160 and the second flexible substrate 170 have a length long enough to avoid the influence of heat generated by the first high-frequency electrode 266 obviates the need to consider the heat resistance of the heater member conducting lines 2681 and 2684 and of the first high-frequency electrode conducting line 266*b*. In addition, the embodiment can obtain the same effects as those of the first embodiment, for example, ease of routing, concerning the heater member conducting lines 2681 and 2684 and the first high-frequency electrode conducting line 266*b*.

Like the first and second embodiments, this embodiment may be configured to perform heating control for the heater members 301 and 304, the heater members 302 and 305, and the heater members 303 and 306, i.e., each zone, by providing wires for each zone.

Note that the present invention is not limited to each embodiment described above, and constituent elements can be modified and embodied in the execution stage within the spirit and scope of the invention. In addition, various inventions can be formed by proper combinations of a plurality of constituent elements disclosed in the above embodiments. Furthermore, constituent elements in different embodiments may be combined as needed. For example, the arrangement of the first high-frequency electrode 266 and the arrangement of the second high-frequency electrode 270 can be those in different embodiments.

Additional advantages and modifications will readily occur to those skilled in the art. Therefore, the invention in its broader aspects is not limited to the specific details and representative embodiments shown and described herein. Accordingly, various modifications may be made without departing from the spirit or scope of the general inventive concept as defined by the appended claims and their equivalents.

What is claimed is:

1. A medical treatment apparatus comprising:
   a heat conduction plate configured to extend along a longitudinal axis;
   an electric resistance pattern comprising a winding portion and a first conductive plate portion, the electric resistance pattern being configured to overlap the heat conduction plate and to generate heat applied to a living tissue through the heat conduction plate; and
   a printed wiring board attached to the heat conduction plate, the printed wiring board comprising:
      a proximal portion configured to extend along the longitudinal axis from a proximal end of the heat conduction plate;
      at least one land printed on the proximal portion; and
      at least one printed pattern comprising a second conductive plate portion, the at least one printed pattern being configured to supply an electric current for generating the heat from the at least one land to the winding electric resistance pattern through the second conductive plate portion and the first conductive plate portion.

2. The medical treatment apparatus according to claim 1, further comprising at least one lead wire connected to the at least one land and configured to supply the electric current.

3. The medical treatment apparatus according to claim 1, wherein the heat conduction plate comprises an electrode configured to apply a high frequency current for treating the living tissue and the heat.

4. The medical treatment apparatus according to claim 3, further comprising a controller configured to:
   control a first generator to generate the high-frequency current; and
   subsequent to generating the high-frequency current, control a second generator to generate the electric current.

5. The medical treatment apparatus according to claim 3, further comprising at least one lead wire connected to an other land printed on the proximal portion and configured to supply an high-frequency electric current to the heat conduction plate.

6. The medical treatment apparatus according to claim 3, further comprising a first insulation layer between the electric resistance pattern and the electrode.

7. The medical treatment apparatus according to claim 1, further comprising a second insulation layer on the electric resistance pattern.

8. The medical treatment apparatus according to claim 1, further comprising an other electric resistance pattern which is identical with the electric resistance pattern.

9. The medical treatment apparatus according to claim 8, wherein the heat conduction plate comprising a first side portion and a second side portion disposed across the longitudinal axis from the first side portion,
   the electric resistance pattern is disposed over the first side portion, and
   the other electric resistance pattern is disposed over the second side portion.

10. The medical treatment apparatus according to claim 8, wherein the other electric resistance pattern is provided side by side to the electric resistance pattern along the longitudinal axis.

11. The medical treatment apparatus according to claim 1, wherein the first conductive plate portion having a first width in a width direction perpendicular to the longitudinal axis, and
   the proximal portion having a second width in the width direction larger than the first width.

12. The medical treatment apparatus according to claim 1, wherein the at least one land is larger in area than the first conductive plate portion.

13. The medical treatment apparatus according to claim 1, further comprising
- a fixed jaw comprising the heat conduction plate, the electric resistance pattern, and the printed wiring board, and
- a rotatable jaw configured to rotate against the fixed jaw.

14. The medical treatment apparatus according to claim 13, further comprising
- an elongated member attached to the fixed jaw, and
- a support pin configured to connect the rotatable jaw with the elongated member,
- wherein the proximal end of the printed wiring board is disposed at a proximal position of the support pin.

15. The medical treatment apparatus according to claim 1, further comprising a cutter configured to cut the living tissue in response to finishing coagulation of the living tissue.

16. The medical treatment apparatus according to claim 1, wherein the winding portion is configured to extend along the longitudinal axis.

17. The medical treatment apparatus according to claim 1, wherein the electric resistance pattern is configured to be controlled between 100 to 300 degrees Celsius.

* * * * *